United States Patent
Kurome et al.

(10) Patent No.: US 6,787,032 B2
(45) Date of Patent: Sep. 7, 2004

(54) DIALYSIS LIQUID PREPARING APPARATUS

(75) Inventors: Kanji Kurome, Hino (JP); Ken Imai, Hino (JP); Tsuneo Deguchi, Hino (JP)

(73) Assignee: Teijin Limited, Osaka (JP)

( * ) Notice: Subject to any disclaimer, the term of this patent is extended or adjusted under 35 U.S.C. 154(b) by 0 days.

(21) Appl. No.: 10/049,232

(22) PCT Filed: Jun. 12, 2001

(86) PCT No.: PCT/JP01/04976
§ 371 (c)(1),
(2), (4) Date: Feb. 11, 2002

(87) PCT Pub. No.: WO01/95954
PCT Pub. Date: Dec. 20, 2001

(65) Prior Publication Data
US 2002/0134721 A1 Sep. 26, 2002

(51) Int. Cl.$^7$ .............................................. B01D 61/26
(52) U.S. Cl. ............................... 210/257.1; 210/257.2; 141/329; 215/302; 220/277; 222/80
(58) Field of Search ......................... 210/257.1, 257.2, 210/321.71, 321.84, 348, 646, 647; 141/329, 330; 215/301, 302; 220/277; 222/80, 81, 83, 541.2; 422/261, 262, 264, 266; 137/268; 366/150.1, 151.1, 151.2

(56) References Cited

U.S. PATENT DOCUMENTS

| | | | | |
|---|---|---|---|---|
| 4,664,891 A | * | 5/1987 | Cosentino et al. | 422/269 |
| 4,784,495 A | | 11/1988 | Jonsson et al. | 366/151 |
| 5,547,645 A | | 8/1996 | Ego et al. | 422/264 |
| 5,788,099 A | * | 8/1998 | Treu et al. | 215/230 |
| 5,932,110 A | * | 8/1999 | Shah et al. | 210/739 |

FOREIGN PATENT DOCUMENTS

| | | |
|---|---|---|
| JP | 4-84967 | 3/1992 |
| JP | 5-168678 | 7/1993 |
| JP | 2753242 | 2/1996 |
| JP | 8-280792 | 10/1996 |
| JP | 9-618 | 1/1997 |
| JP | 30252004 | 1/2000 |
| JP | 2000-296175 | 10/2000 |
| WO | WO 96/25214 | 8/1996 |
| WO | WO 00/37127 | 6/2000 |
| WO | WO 01/60428 | 8/2001 |

* cited by examiner

Primary Examiner—Joseph Drodge
(74) Attorney, Agent, or Firm—Rader, Fishman & Grauer PLLC

(57) ABSTRACT

An apparatus for preparing dialysis liquid includes a container holder 112 for holding an inverted container 102, the container having a tubular body portion which accommodates a powder preparation, a bottom wall, and a sealing member for closing an outlet opening defined at the end of the tubular body portion opposite to the bottom wall. The apparatus also includes a movable cutter 118 for cutting the sealing member, a mesh member 116, horizontally disposed above the tank, for receiving the powder preparation from the container 102, and a nozzle 120 for applying water to the powder preparation which has fallen on the mesh member after the sealing member is cut by the cutter 118. The water and powder are received in a concentrated liquid tank 114*a* provided under the container holder 112, and the concentrated liquid is diluted with a diluting water as it is supplied to the dialyzer 160.

6 Claims, 4 Drawing Sheets

DIALYSIS LIQUID PREPARING APPARATUS

This application is a 371 of PCT/JP01/04976, filed Jun. 12, 2001 and claims priority to Japanese application JP 2000-174,997, filed Jun. 12, 2000.

TECHNICAL FIELD

The invention relates to an apparatus for preparing dialysis a liquid which is used for hemodialysis.

BACKGROUND ART

Hemodialysis is an effective treatment for renal insufficiency. Hemodialysis consists of circulating blood and dialysis liquid through a hollow fiber semi-permeable module that uses a polymer membrane made of cellulose or polysulfone, and so forth, to remove waste products and excess water from the blood. The dialyzed blood is returned to the patient. Dialysis liquid is prepared from an acetic acid based preparation (A Preparation) and bicarbonate based preparation (B Preparation). The preparation is available commercially in the form of a concentrated liquid including dextrose, sodium chloride, potassium chloride, calcium chloride, magnesium chloride, acetic acid and so forth. The B preparation available commercially in the form of powders including sodium bicarbonate and sodium chloride. As a dialysis liquid preparing apparatus, for automatically preparing a dialysis liquid, Japanese Unexamined Patent Publications (Kokai) No. 9-618 and No. 4-84967 describe an apparatus which injects water into a bottle in which a powder is sealed, allows the entire amount to flow into a tank, and stirs and mixes the solution in a tank equipped with a stirrer, as well as an apparatus that mixes using a circulating pump.

Further, Japanese Unexamined Patent Publication (Kokai) No. 5-168678 describes an apparatus which holds a quantitative powder container in the inverted state, allows the powder to drop naturally into a tank, and then stirs and mixes the powder in the tank.

Normally, 0.12 $m^3$ of dialysis liquid is required for a four-hour dialysis. Therefore, a relatively large tank of, or larger than, 0.12 $m^3$ is required for such a prior art dialysis liquid preparing apparatus which results in an increase in the volume of the apparatus and its complex piping system.

On the other hand, contamination of the dialysis liquid preparation apparatus and the dialysis liquid supply lines leads to bacterial growth in the lines which causes fever in patients due to endotoxins. It is therefore necessary to clean and sterilize the dialysis liquid preparing apparatus and the dialysis liquid supply lines before and after use as well as the dialyzer itself. Thus, an arrangement facilitating the cleaning and sterilization of the apparatus is important for a dialysis liquid preparing apparatus and the stirrer and the complex piping system results in a relatively long time for cleaning and sterilizing the apparatus.

Further, Japanese Patent No. 2753242 describes a dialysis liquid preparing apparatus which supplies water to a sealed cartridge of a solid preparation for preparing dialysis liquid to remove the dissolved concentrated liquid. For the dialysis liquid preparing apparatus, special cartridges with powder enclosed must be produced. Further, according to the method disclosed in the publication, it is difficult to keep the concentration of the prepared concentrated dialysis liquid constant. In order to solve this problem, the concentrated dialysis liquid must be removed as a saturated solution so that an amount of powder preparation more than the amount necessary for one dialysis must be filled in the cartridge.

DISCLOSURE OF THE INVENTION

The invention is directed to solve the problems of the prior art, and to provide a dialysis liquid preparing apparatus which realizes a simple constitution by eliminating the tank, which occupies a substantial portion of the apparatus, to reduce the volume of the apparatus. The apparatus is also improved sanitarily by completely using one prescribed amount of the preparation.

Further, the object of the inventions is to provide an economical dialysis liquid preparing apparatus which allows one prescribed amount of the powder preparation for preparing dialysis liquid to be dissolved in a short time to prepare a concentrated dialysis liquid of a constant concentration.

According to the invention, an apparatus for preparing dialysis liquid which comprises a container holder for holding a container in the inverted state, the container having a tubular body portion which defines an internal volume for accommodating powder preparation for preparing dialysis liquid, a bottom wall defined at an end of the tubular body portion, and a sealing member for closing an outlet opening defined at the end of the tubular body portion opposite to the bottom wall, a cutter, movable toward and away from the sealing member, for cutting the sealing member, a concentrated liquid tank provided under the container holding means, a mesh member, horizontally disposed above the tank, for receiving the powder preparation which has fallen from the container and a nozzle for applying water to the powder preparation for preparing dialysis liquid which has fallen on the mesh member from the container after the sealing member is cut by the cutter. The water is applied to the powder preparation for preparing dialysis liquid dropped on the mesh member to produce a concentrated liquid for the dialysis liquid, which is received in the concentrated liquid tank, and the concentrated liquid is diluted with diluting water as it is supplied to the dialyzer.

In the dialysis liquid preparing apparatus of the invention, a large tank can be eliminated by preparing a dialysis liquid of a predetermined concentration by diluting a concentrated dialysis liquid of a predetermined concentration with water. The dialysis liquid preparing apparatus of the present invention do not require a large tank. Therefore, the amount of water and electricity necessary for cleaning and sterilization of the apparatus are considerably decreased compared with, for example, the batch type dialyzer having a dialysis liquid preparing apparatus and a large tank disclosed in Japanese Unexamined Patent Publication (Kokai) No. 9-618.

Further, the apparatus of the invention can dissolve one unit of prescribed amount of powder preparation within a short time to prepare the concentrated liquid and uses a new bottle for each treatment. Therefore, it is economically and sanitarily improved. Further, the apparatus of the invention allows cleaning and sterilization to be executed easily by circulating hot water through the apparatus. The simple configuration of the dissolving apparatus facilitates the cleaning, which improves the apparatus sanitarily.

BEST MODE FOR CARRYING OUT THE INVENTION

The preferred embodiments of the present invention will be described below.

Figure 1:
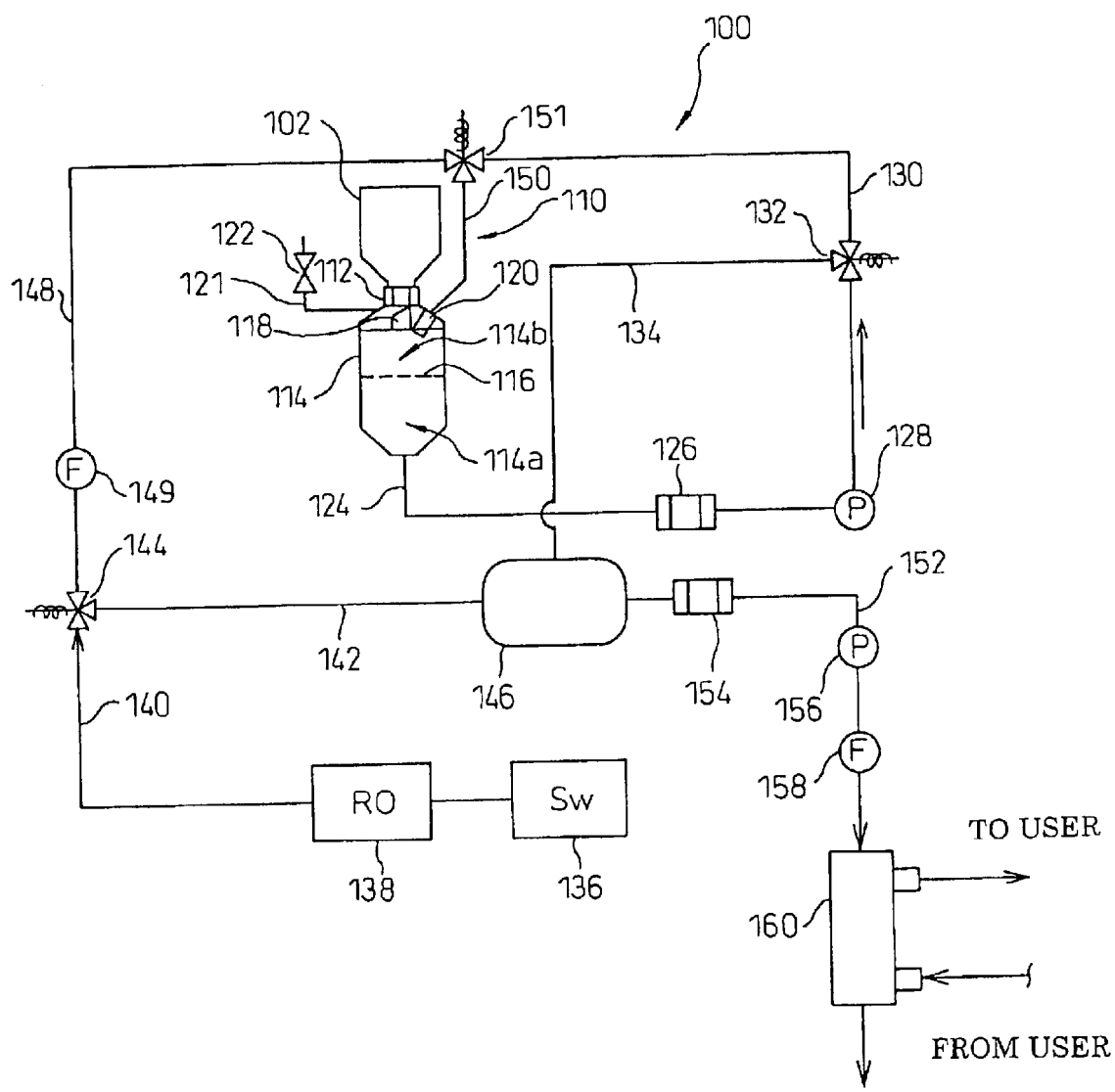
FIG. 1 is a schematic diagram of a dialysis liquid preparing apparatus according to the first embodiment of the invention.

First, referring to FIG. 1, a dialysis liquid preparing apparatus 100 of a first embodiment includes a powder preparation dissolving apparatus 110. The powder preparation dissolving apparatus 110 has a dissolving chamber 114 disposed at a lower portion thereof. Provided at the top end of the dissolving chamber 114 is a container holder 112 for holding a container 102, in the inverted state, which is filled with powder preparation for preparing dialysis liquid, in particular the B preparation. The container 102 includes a tubular main body for accommodating the powder preparation for preparing dialysis liquid, in particular the B preparation, a bottom wall defined at one end of the main body, a sealing member for sealingly closing an outlet opening which is defined at the end of the tubular member opposite to the bottom wall.

Within the dissolving chamber 114, a cutter 118 is movable toward and away from the sealing member (not shown) at the outlet of the container 102 held by the container holder 112. The cutter 118 is referred to as a spike and has a cylindrical body and a cutting edge, provided at the top end of the body, for cutting the sealing member of the container 102 along the periphery of the outlet opening. The details of the cutter 118 is described in PCT/JP99/07165 which is incorporated by reference.

Further, a mesh member 116 is horizontally provided in the dissolving chamber 114 to cross the internal volume of the dissolving chamber 114. The mesh member 116 separates the internal volume of the dissolving chamber 114 into an upper volume 114b above the mesh member 116 and a lower volume 114a under the mesh member 116. The lower volume defines a concentrated liquid tank. The concentrated liquid tank 114a is fluidly connected to a circulation pump 128 through an outlet conduit 124 provided at the lower end thereof. A circulation conduit 130 is connected to the outlet port (not shown) of the circulation pump 128. The circulation conduit 130 is connected to an inlet conduit 150 through a three way valve 151. A nozzle 120 is attached to the end of the inlet conduit 150 and oriented toward the mesh member 116. The nozzle 120 may be any type of nozzle which allows, as described below, RO water to be directed toward the mesh member 116 and, although the number of the ports is not limited, preferably, a plurality of ports are provided to promote the effect. Regarding the direction of the RO water supply, the RO water is preferably sprayed over the entire surface of the mesh member 116 from the above of the mesh member 116.

A concentrated liquid supply conduit 134 is connected to the circulation conduit 130 through a three way valve 132. The end of the concentrated liquid supply conduit 134 opposite to the three way valve 132 is connected to a mixing portion 146. The three way valve 132 may be a solenoid valve which is movable between a first position at which the fluid communication is established through the circulation conduit 130 between the upstream and downstream sides of the three way valve 132, and a second position at which the circulation conduit 130 upstream of the three way valve 132 is fluidly connected to the concentrated liquid supply conduit 134.

A vent valve 122, for equalizing the internal pressure of the dissolving chamber 114 to the external pressure, is connected to the dissolving chamber 114.

Water, which is necessary for the process for dissolving the powder preparation executed in the powder preparation dissolving apparatus 110, is supplied from a RO water source 138. The RO water source 138 is a water treatment apparatus which produces RO water (Reverse Osmosis water) by pressurizing and forcing raw water from a raw water source 136, such as a city water system, through a reverse osmosis membrane (not shown) to remove particles, bacteria and ions. The RO water source 138 is connected to the inlet conduit 150 through a RO water outlet conduit 140, a three way valve 144, a RO water supply conduit 148 and the three way valve 151. The three way valve 151 may be a solenoid valve which is movable between a first position at which the RO water supply conduit 148 is fluidly connected to the inlet conduit 150, and a second position at which the circulation conduit 130 is fluidly connected to the inlet conduit 150. The RO water outlet conduit 140 is further connected to a diluting water conduit 142 through the three way valve 144. The end of the diluting water conduit 142 opposite to the three way valve 144 is connected to the mixing portion 146. The three way valve 144 may be a solenoid valve which is movable between a first position at which the RO water outlet conduit 140 is fluidly connected to the RO water supply conduit 148, and a second position at which the RO water outlet conduit 140 is fluidly connected to the diluting water conduit 142.

The mixing portion 146 may comprise a tubular member having two inlet ports (not shown) and an outlet port (not shown). The concentrated liquid supply conduit 134 and the diluting water conduit 142 are connected to the inlet ports. A dialysis liquid supply conduit 152 is connected to the outlet port of the mixing portion 146. The dialysis liquid supply conduit 152 is connected to a dialyzer 160 through a conductivity meter 154, a dialysis liquid supply pump 156 and a flow meter 158.

The operation of this embodiment will be described below.

When a dialysis liquid is prepared, the container 102, filled with a powder preparation, is first mounted to the dialysis liquid preparing apparatus 100 by securing it to the container holder 112 in the inverted state, i.e., the opening is positioned at the bottom. Next, the cutter 118 moves toward the opening of the container 102 to cut the sealing member which closes the opening. This allows the powder preparation in the container 102 to drop naturally to the top of the mesh member 116. Subsequently, the three way valves 144 and 151 are moved to their first positions to fluidly connect the RO water source 138 to the inlet conduit 150 so that the RO water is supplied to the powder preparation on the top of the mesh member 116 through the nozzle 120 provided at the end of the inlet conduit 150. This allows the powder preparation on the mesh member 116 to be dissolved into the RO water and the solution thereof to be received in the concentrated liquid tank 114a provided under the mesh member 116.

Although the concentrated liquid tank 114a is preferably as small as possible, if the volume of dissolution water is too small, a long time is required for dissolution. In this connection, if the concentrated liquid is prepared at the saturated concentration, a small change in the environment may result in precipitation of the preparation. Therefore, the amount of RO water supply is preferably, depending on the prescription, at least an amount which provides a concentration of the concentrated liquid equal to or lower that 6/7 of the saturation and at most an amount which provides a concentration of the concentrated liquid equal to or higher that 1/7 of the saturation. For example, in the case of bicarbonate dialysis, in order to produce a dialysis liquid of 0.12 m$^3$, sodium bicarbonate of 320 g (saturated concentration: 10.3 g/100 g (25° C.)) can be dissolved into 0.0036–0.0217 m$^3$ of water, preferably 0.007 m$^3$ of water to prepare the concentrated liquid. This allows a tank of 0.12 m$^3$, which is required in the prior art, to be eliminated.

The amount of the RO water, supplied from the RO water source 138 to the powder preparation dissolving apparatus 110, is measured by a flow meter 149 provided in the RO water supply conduit 148. When a predetermined amount of the RO water is supplied to the powder preparation dissolving apparatus 110, the supply of the RO water is terminated. Subsequently, the three way valve 132 moves to the first position, the three way valve 151 moves to the second position and the circulation pump 128 is activated. This allows the solution in the concentrated liquid tank 114a to be recirculated through the outlet conduit 124, the circulation pump 128, the circulation conduit 130, the three way valve 151 and the inlet conduit 150 to the concentrated liquid tank 114a. Continuing this process for a predetermined period allows the solution in the concentrated liquid tank 114a to be completely mixed and any undissolved powder preparation, which may be attached to the mesh member 116, to be completely dissolved into the solution whereby a concentrated liquid for the dialysis liquid is produced. A conductivity meter 126, for measuring the conductivity of the solution flowing through the outlet conduit 124, may be provided in the outlet conduit 124 to monitor whether the powder preparation has been sufficiently dissolved into the RO water.

When the powder preparation and the RO water is mixed uniformly and the concentrated dialysis liquid is produced, the three way valves 132 and 144 move to the respective second positions to fluidly connect the circulation conduit 130 and the RO water outlet conduit 140 to the mixing portion 146. This allows the RO water to be supplied to the mixing portion 146, as diluting water from the RO water source 138. In this connection, according to the embodiment, the diluting water is supplied from the RO water source 138 under the pressure of the city water system. However, an additional pump, for increasing the pressure of the diluting water, may be provided in the RO water source 138 or the raw water source 136.

Subsequently, the dialysis liquid supply pump 156 is activated to supply the dialysis liquid from the mixing portion 146 to the dialyzer 160 through the dialysis liquid supply conduit 152. The flow rate of the dialysis liquid supplied to the dialyzer 160 is measured by the flow meter 158, provided in the dialysis liquid supply conduit 152, to control the dialysis liquid supply pump 156, based on the measurement results by the flow meter 158, so that the flow rate of the dialysis liquid through the dialysis liquid supply conduit 152 becomes a predetermined value. Further, the flow rate of the concentrated liquid supplied by the circulation pump 128 to the mixing portion 146 is controlled based on value measured by the conductivity meter 154, provided in the dialysis liquid supply conduit 152, so that the conductivity of the dialysis liquid through the dialysis liquid supply conduit 152 becomes a predetermined value.

According to the embodiment, the entire amount of the powder preparation can drop naturally on the mesh member 116 by holding the container 102, filled with the powder preparation, in the inverted state and cutting the sealing member along the periphery of the opening. The powder preparation on the mesh member 116 is dissolved into the RO water supplied onto the powder preparation on the mesh member 116 so that the solution passes through the mesh member 116 into the concentrated liquid tank 114a provided under the mesh member 116. The mesh size is preferably equal to or smaller than 150 μm because if the size is too large, the powder preparation may not be held and may flow into the tank as crystals or a powder. On the other hand, the mesh size is preferably equal to or larger than 20 μm because the smaller the mesh size, the worse the permeability for the solution so that a longer the time for dissolution is required.

The entire amount of the powder preparation can be dissolved by circulating the solution in the concentrated liquid tank 114a for a predetermined period. Thus, a concentrated liquid of a predetermined concentration can be produced by measuring the flow rate of the RO water supplied to the dialysis liquid preparing apparatus 100, which concentrated liquid is diluted by the RO water from the RO water source 138 so that a dialysis liquid of a predetermined concentration is supplied to the dialyzer 160. The conductivity of the dialysis liquid is measured by the conductivity meter 154, provided in the dialysis liquid supply conduit 152, to control the flow rate of the concentrated liquid to the mixing portion 146 so that the conductivity becomes a predetermined value. This allows the concentration of the dialysis liquid supplied to the dialyzer 160 to be maintained at a predetermined value. As described above, according to the first embodiment, the entire amount of the powder preparation can be dissolved into the RO water without an agitator tank which is required in the prior art, and the dialysis liquid of a predetermined concentration can be supplied to the dialyzer 160.

Next, a second embodiment of the present invention will be described with reference to FIG. 2.

A dialysis liquid preparing apparatus 200 according to the second embodiment includes, in addition to the powder preparation dissolving apparatus 110, a liquid preparation diluting apparatus 210 for diluting and preparing liquid preparation, in particular, the A preparation. The rest of the constitution is the same as the first embodiment and, in FIG. 2, the elements similar to those in FIG. 1 are indicated by the same reference numbers.

Figure 2:
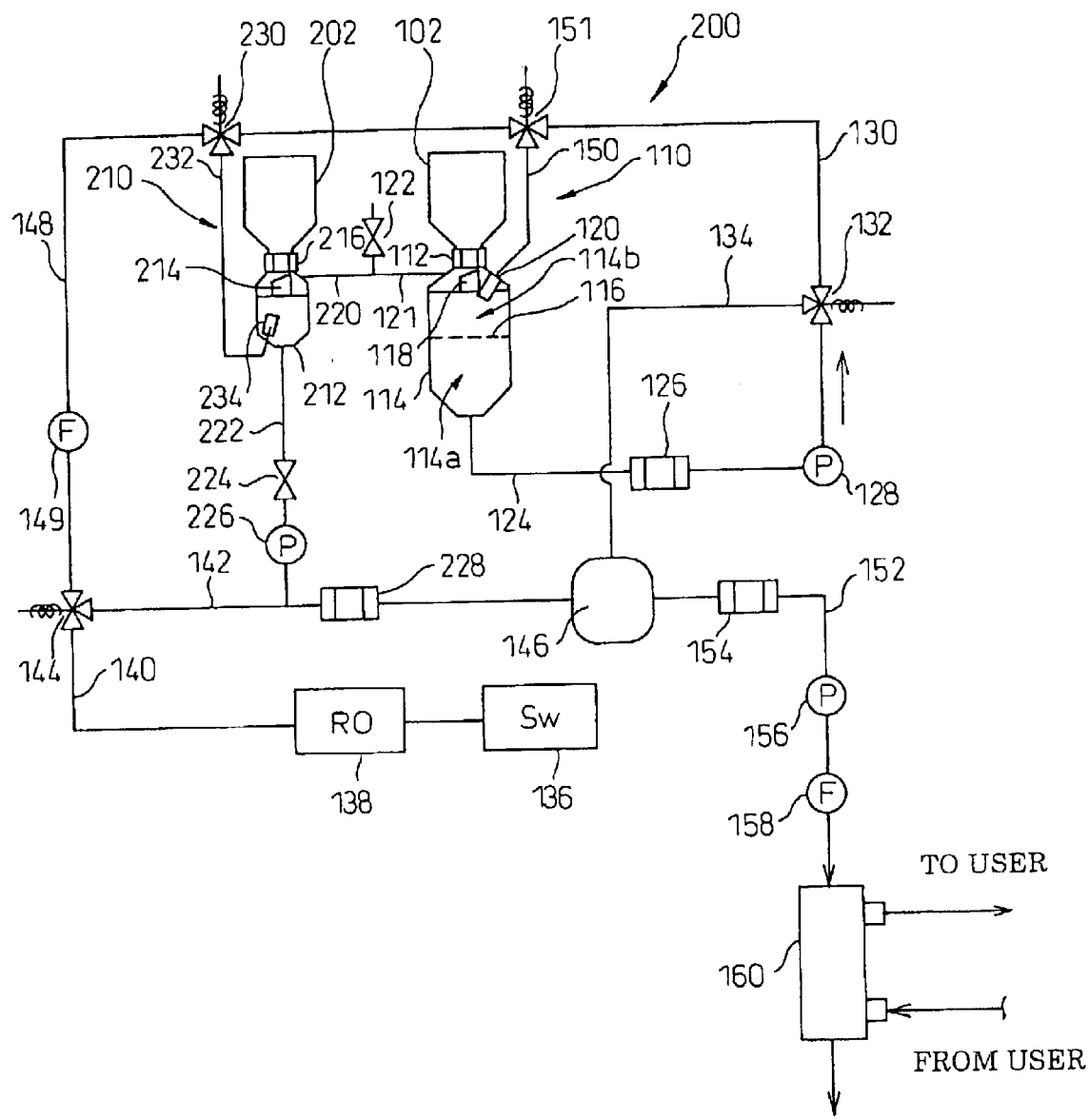
FIG. 2 is a schematic diagram of a dialysis liquid preparing apparatus according to the second embodiment of the invention.

Referring to FIG. 2, the liquid preparation diluting apparatus 210 includes a liquid preparation tank 212 which is provided at a lower portion thereof. Provided at the top end of the liquid preparation tank 210 is a container holder 216, for holding a container 202 in the inverted state, which is filled with liquid preparation for preparing dialysis liquid and, in particular, the A preparation. Within the liquid preparation tank 212, a cutter 214 is movable toward and away from a sealing member (not shown) provided at the outlet of the container 202 held by the container holder 216. The cutter 214 can comprise a cutter similar to the cutter 118 of FIG. 1. The liquid preparation tank 212 is fluidly connected, through a vent conduit 220, to the vent valve 122 which is common to the powder preparation dissolving apparatus 110.

The liquid preparation tank 212 is fluidly connected to a diluting liquid supply conduit 142 through an outlet conduit 222. A liquid preparation supply pump 226, for adjusting the flow rate of the liquid preparation supplied to the diluting liquid supply conduit 142, is connected to the outlet conduit 222. Further, a conductivity meter 228 is provided in the diluting liquid supply conduit 142 upstream of the mixing portion 146.

The operation of the second embodiment will be described below.

According to the second embodiment, the powder preparation (B Preparation) is dissolved into the RO water and the concentrated liquid is received in the concentrated liquid tank 114a, as in the first embodiment. The container 202, which is filled with a liquid preparation and, in particular the A preparation, is held by the container holder 216 in the inverted state, and the cutter 214 moves toward the outlet opening to cut the sealing member (not shown) closing the outlet opening. This allows the liquid preparation to fall naturally into the liquid preparation tank 212 and to be held therein. The liquid preparation in the liquid preparation tank 212 is mixed, by the liquid preparation supply pump 226 and at a predetermined rate, with the RO water which flows through the diluting water conduit 142. The conductivity meter 228 measures the conductivity of the solution flowing through the diluting water conduit 142 to control the rate of supply of the liquid preparation by the liquid preparation supply pump 226 so that the conductivity value becomes a predetermined value.

Next, referring to FIG. 3, a third embodiment of the present invention will be described.

Figure 3:
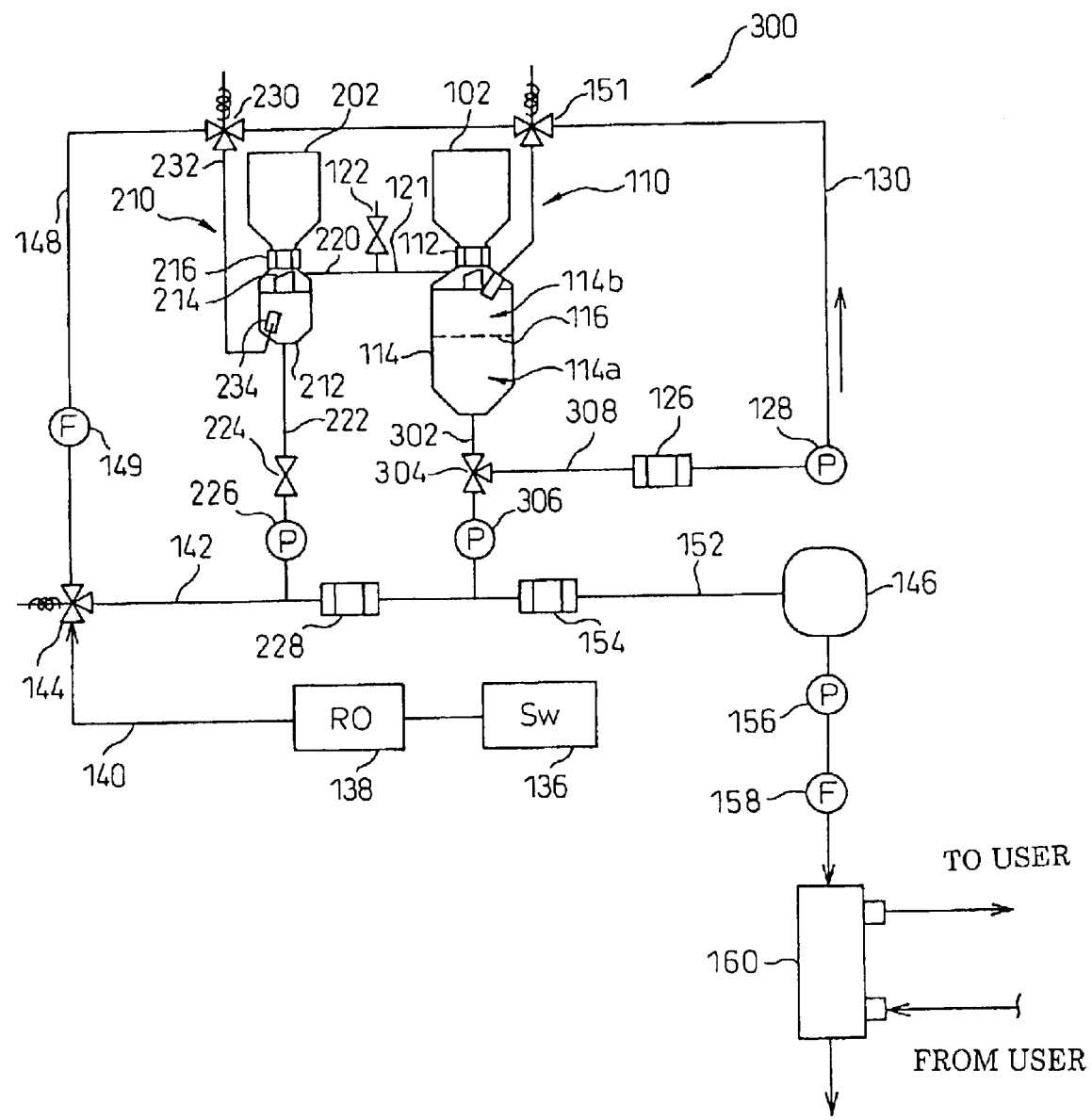
FIG. 3 is a schematic diagram of a dialysis liquid preparing apparatus according to the third embodiment of the invention.

Although, in the first and second embodiment, the concentrated liquid is supplied to the mixing portion 146 by the circulation pump 128, the third embodiment shown in FIG. 3 is provided with an additional pump separated from the circulation pump 128. The rest of the constitution is the same as the second embodiment and, in FIG. 3, the elements similar to those in FIG. 2 are indicated by the same reference numbers.

Referring to FIG. 3, in a dialysis liquid preparing apparatus 200 according to the third embodiment, an outlet conduit 302 is connected to the concentrated liquid tank 114a. The end of the outlet conduit 302 opposite to the concentrated liquid tank 114a is connected to the dialysis liquid supply conduit 152. A three way valve 304 is provided in the outlet conduit 302, and a concentrated liquid supply pump 306 is provided in the outlet conduit 302 downstream of the three way valve 304. Further, the outlet conduit 302 is connected to a circulation pump inlet conduit 308 through the three way valve 304. The circulation pump inlet conduit 308 is connected to an inlet port (not shown) of the circulation pump 128. Further, a conductivity meter 126 is provided in the circulation pump inlet conduit 308. The three way valve 304 may be a solenoid operated valve which is movable between a first position at which the fluid communication is established through the outlet conduit 302 between the upstream and downstream sides of the three way valve 132, and a second position at which the outlet conduit 302 upstream of the three way valve 304 (the side adjacent the concentrated liquid tank 114a) is fluidly connected to the circulation pump inlet conduit 308.

The operation of the third embodiment will be described below.

According to this embodiment, the solution in the concentrated liquid tank 114a is circulated by moving the three way valve 304 to the second position to promote the mixing and dissolution of the powder preparation with and into the RO water. When the process for mixing and dissolving of the powder preparation with and into the RO water is completed, the three way valve 304 is moved to the first position and the concentrated liquid supply pump 306 is activated. This allows the concentrated liquid held in the concentrated liquid tank 114a to be supplied to the dialysis liquid supply conduit 152 so that the concentrated liquid is supplied to the dialyzer 160 along with the liquid preparation from the liquid preparation diluting apparatus 210. At that time, the conductivity of the dialysis liquid flowing through dialysis liquid supply conduit 152 is measured by the conductivity meter 154 to control the flow rate of supply of the concentrated liquid supplied by the concentrated liquid supply pump 306 so that the measured value becomes a predetermined value. In this embodiment, a mixing portion 310, for mixing the solution of the A preparation and the B preparation, is provided in the dialysis liquid supply conduit 152 downstream of the conductivity meter 154.

Next, referring to FIG. 4, a fourth embodiment of the present invention will be described below.

In the third embodiment, both the concentrated liquid from the concentrated liquid tank 114a and the liquid preparation from the liquid preparation diluting apparatus 210 are supplied to the dialysis liquid supply conduit 152, and the mixing of the liquid and the diluting water is promoted in the mixing portion 310. The invention is not limited to this configuration and separated mixing portions may be respectively provided for the concentrated liquid from the concentrated liquid tank 114a and the liquid preparation from the liquid preparation diluting apparatus 210, as shown in FIG. 4. The rest of the constitution is the same as the third embodiment and, in FIG. 4, the elements similar to those in FIG. 3 are indicated by the same reference numbers.

Figure 4:
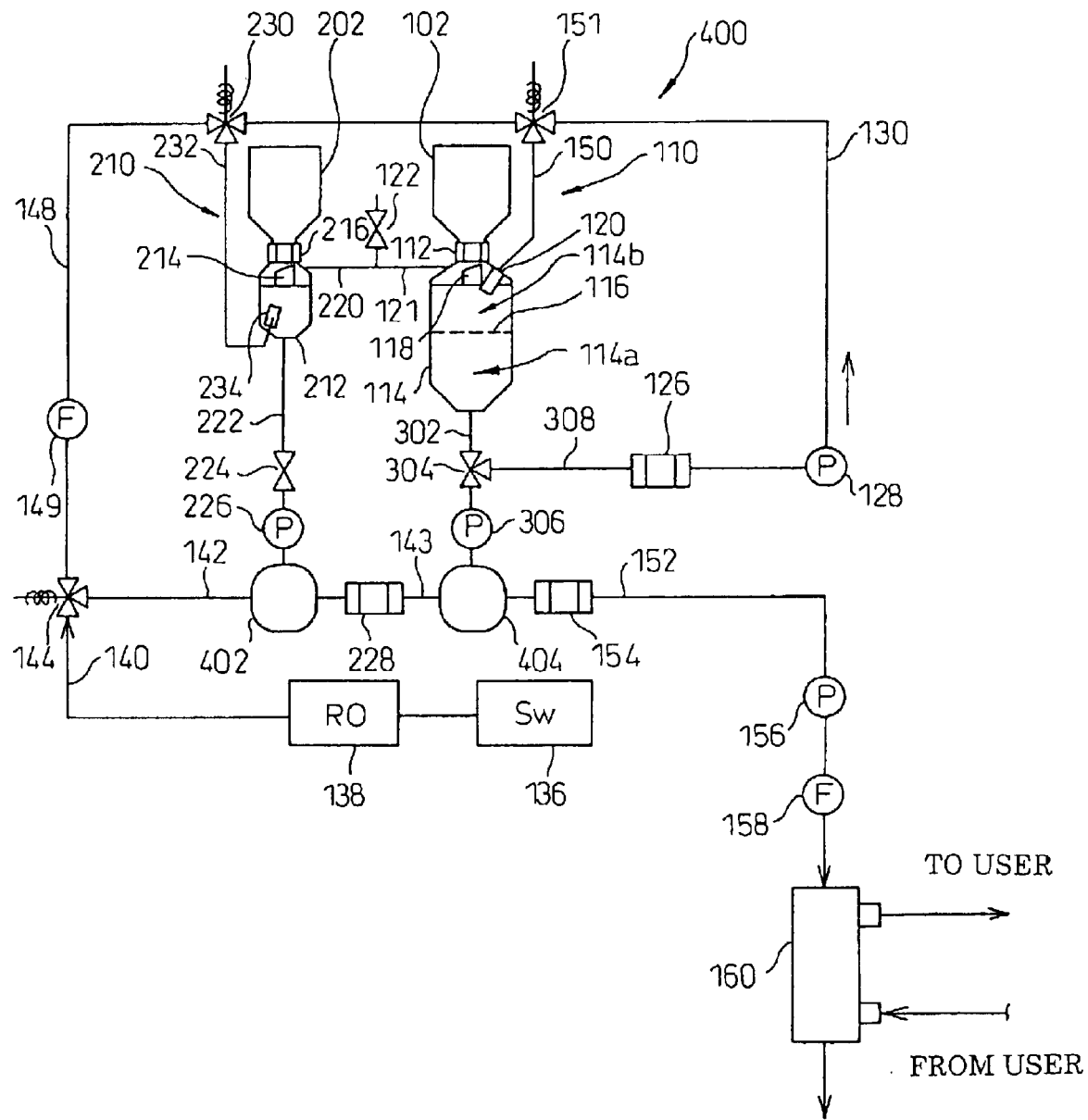
FIG. 4 is a schematic diagram of a dialysis liquid preparing apparatus according to the fourth embodiment of the invention.

Referring to FIG. 4, in a dialysis liquid preparing apparatus 400 according to the fourth embodiment, mixing portions 402 and 404 are provided in the dialysis liquid supply conduit 152. The mixing portion 402 can comprise a tubular member having two inlet ports (not shown) and an outlet port (not shown). The outlet conduit 222 from the liquid preparation tank 212 and the diluting water conduit 142 are connected to the inlet ports and an intermediate conduit 143 is connected to the outlet port. The intermediate conduit is provided with the conductivity meter 228 for measuring the conductivity of the diluted liquid preparation.

The mixing portion 404 can also comprise a tubular member having two inlet ports (not shown) and an outlet port (not shown). The intermediate conduit 143 from the mixing portion 402 and the outlet conduit 302 from the concentrated liquid tank 114a are connected to the inlet ports and the dialysis liquid supply conduit 152 is connected to the outlet port. The dialysis liquid supply conduit 152 is connected to the dialyzer 160 through the conductivity meter 154, the dialysis liquid supply pump 156 and the flow meter 158.

The configuration of the separate mixing portions 402 and 404, which are respectively provided for the concentrated liquid from the concentrated liquid tank 114a and the liquid preparation from the liquid preparation diluting apparatus 210, and the conductivity meters 228 and 154, which are provided at the downstream of the mixing portions 402 and 404 respectively, allows the rates of supply of the liquid preparation and the concentrated liquid, by the liquid preparation supply pump 226 and concentrated liquid supply pump 306, to be controlled separately so that the measured values of the conductivity meters 228 and 154 become predetermined values. Therefore, the rates of supply of the liquid preparation and the concentrated liquid can be controlled precisely more than in the third embodiment.

What is claimed is:

1. An apparatus for preparing dialysis liquid, comprising:
   a container holder holding a container in the inverted state, the container having a tubular body portion which defines an internal volume for accommodating powder preparation for preparing a dialysis liquid, a bottom wall defined at an end of the tubular body portion, and a sealing member for closing an outlet opening defined at the end of the tubular body portion opposite to the bottom wall;

a cutter, movable toward and away from the sealing member, for cutting the sealing member;

a concentrated liquid tank provided under the container; holder a mesh member, horizontally disposed above the tank, for receiving the powder preparation which has fallen from the container;

a nozzle oriented, for applying water downward to the powder preparation for preparing dialysis liquid which has fallen on the mesh member from the container after the sealing member is cut by the cutter; and the water being applied, to the powder preparation for preparing dialysis liquid dropped on the mesh member, to produce a concentrated liquid for the dialysis liquid, which is received in the concentrated liquid tank, and the concentrated liquid being diluted with a diluting water as it supplied to the dialyzer.

2. An apparatus for preparing dialysis liquid according to claim 1, wherein the size of the mesh member is 20–150 $\mu$m; and the cutter, including a cylindrical body and a cutting edge provided on the end thereof for cutting the sealing member of the container along the periphery of the outlet opening.

3. An apparatus for preparing dialysis liquid according to claim 1, wherein the water is supplied to an amount providing a concentration, of the solution, which is 6/7 to 1/7 of the saturated concentration of the powder preparation for preparing the dialysis liquid.

4. An apparatus for preparing dialysis liquid according to any one of claims 1 to 3, further comprising a RO water source for producing RO water; and the RO water, produced by the RO water source, being applied to the powder preparation for preparing dialysis liquid dropped on the mesh member.

5. An apparatus for preparing dialysis liquid according to any one of claims 1 to 3, wherein the diluting water is the RO water produced by the RO water source.

6. An apparatus for preparing dialysis liquid according to any one of claims 1 to 3, further comprising a liquid preparation diluting apparatus for diluting the liquid preparation for preparing dialysis liquid and for supplying the diluted solution to the dialyzer.

* * * * *